United States Patent [19]

Campbell et al.

[11] Patent Number: 4,577,044

[45] Date of Patent: Mar. 18, 1986

[54] PREPARATION OF CHLOROTRIFLUOROETHYLENE TELOMERS WITH FLUOROXYTRIFLUOROMETHANE

[75] Inventors: Donald H. Campbell, Niagara-on-the-Lake, Canada; Michael J. Fifolt; Mohan S. Saran, both of Grand Island, N.Y.

[73] Assignee: Occidental Chemical Corporation, Niagara Falls, N.Y.

[21] Appl. No.: 700,209

[22] Filed: Feb. 11, 1985

Related U.S. Application Data

[62] Division of Ser. No. 545,020, Oct. 24, 1983.

[51] Int. Cl.$^4$ .................... C07C 41/06; C07C 179/00
[52] U.S. Cl. ................................. 568/677; 568/683; 568/684; 570/139; 570/142
[58] Field of Search ............. 568/677, 684, 683; 570/142, 139

[56] References Cited

U.S. PATENT DOCUMENTS 2,831,035 4/1958 Tyczkowski et al. ............. 570/161
3,099,695 7/1963 Muray ................................ 570/161

OTHER PUBLICATIONS

Allison et al., J.A.C.S., 81, pp. 1089–1091, (1959).
Cady, Proceedings of the Chemical Society, (1960), pp. 133–137.

Primary Examiner—Howard T. Mars
Attorney, Agent, or Firm—James F. Tao; William G. Gosz

[57] ABSTRACT

Telomers formed by reacting chlorotrifluoroethylene with fluoroxytrifluoromethane are disclosed. The telomerization reaction is conducted in either liquid chlorotrifluoroethylene without a solvent or in solution. The telomers thus formed can optionally be fluorinated by reaction with a suitable fluorinating agent to improve their stability.

10 Claims, No Drawings

PREPARATION OF CHLOROTRIFLUOROETHYLENE TELOMERS WITH FLUOROXYTRIFLUOROMETHANE

This is a division of application Ser. No. 545,020 filed Oct. 24, 1983.

BACKGROUND OF THE INVENTION

The present invention relates to novel telomers formed by the reaction of chlorotrifluoroethylene, herinafter designated as "CTFE", with fluoroxytrifluoromethane, hereinafter designated as "FTM". These telomers have properties which distinguish them from other CTFE telomers and make them commercially attractive products. Such properties include superior solvent characteristics which are useful in formulating non-flammable hydraulic fluids.

Various methods of preparing telomers from CTFE are known in the prior art and have been practiced commercially for many years.

An article by William T. Miller, Jr. et al in *Industrial and Engineering Chemistry*, pages 333-337 (1947), entitled "Low Polymers of Chlorotrifluoroethylene", describes a process for producing low molecular weight polymers of CTFE by carrying out the polymerization in a solution of chloroform using benzoyl peroxides as polymerization promoters. Other solvents disclosed in the reference as being useful for this purpose include carbon tetrachloride and tetrachloroethylene. The solution is heated in a pressure vessel for 1¾ hours at 100° C., and the unreacted CTFE monomer and chloroform are removed by distillation, leaving a "crude" telomer of general formula $CHCl_2(CF_2CClF)_nCl$, which can further heated and distilled to yield products ranging from a light oil to a semisolid wax or grease. In this formula, n is the chain length (the number of repeating units in the telomer chain), and is in the range of 1 to 20.

A more recent development in this field is described in a series of articles by Y. Pietrasanta et al. entitled "Telomerization by Redox Catalysis" appearing in the *European Polymer Journal*, Vol. 12 (1976). This technology involves the reaction of a chlorinated telogen, such as carbon tetrachloride, with CTFE in the presence of benzoin and a suitable redox catalyst, such as ferric chloride hexahydrate ($FeCl_3.6H_2O$). The telomerization reaction is suitably carried out in acetonitrile which is a common solvent for the reactants and catalysts. The telomerization reaction can be illustrated as follows, wherein n is as defined above:

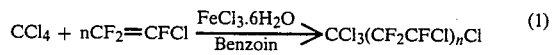

$$CCl_4 + nCF_2=CFCl \xrightarrow[\text{Benzoin}]{FeCl_3.6H_2O} CCl_3(CF_2CFCl)_nCl \quad (1)$$

The telomers produced according to the above-described process have end groups containing chlorine atoms. When used in a particular application, especially high temperature or corrosive applications, the chlorine atoms can be hydrolyzed, which may result in cleavage of the telomer and a loss of physical properties of the fluid. In order to prevent such a condition, the end groups are stabilized by fluorinating the telomer to replace chlorine atoms with fluorine. The fluorine atoms form a stronger bond with carbon and are less prone to cleavage. This results in a fluid which has superior performance over a wider range of operating conditions.

Fluorination of the telomer is accomplished by reaction with a suitable fluorinating agent, such as chlorine trifluoride or hydrogen fluoride. However, fluorination involves an additional process step which increases processing costs. It would be desirable to reduce the amount of fluorination required or eliminate this procedure in its entirey. It would also be desirable to develop superior telomers having imroved physical characteristics, such as better solvent properties. These are the primary objectives of the present invention.

SUMMARY OF THE INVENTION

It has now been found that novel telomers are produced by reacting chlorotrifluoroethylene with fluoroxytrifluoromethane. The reaction can be conducted in liquid chlorotrifluoroethylene without a solvent at a temperature below the boiling point of chlorotrifluoroethylene ($-30°$ C.). Alternatively, the reaction can be conducted in a suitable solvent at somewhat higher temperatures. The novel telomers of this invention are characterized as having at least one trifluoromethoxy ($-OCF_3$) end group.

The telomers produced by this process have improved physical properties as compared to telomers produced by reacting chlorotrifluoroethylene with carbon tetrachloride, or some equivalent telogen, as starting materials.

DESCRIPTION OF THE PREFERRED EMBODIMENTS

The present invention is directed to both processes for producing telomers and the novel telomers produced thereby.

According to the present invention, chlorotrifluoroethylene is reacted with fluoroxytrifluoromethane in liquid CTFE or in solution. If the reaction is conducted in liquid CTFE, a temperature below the boiling point of CTFE, i.e. about $-30°$ C., should be maintained. If high pressure conditions are used, the reaction temperature can be increased to about 100° C. An operable temperature range is therefore from about 100° C. to about $-100°$ C. The absence of a solvent generally entails the use of lower temperatures than a solution telomerization process, but avoids the necessity of separation and purification of the product.

Alternatively, the reaction can be conducted in solution using a solvent, which is inert to fluorine under the reaction conditions. Suitable solvents are generally fluorinated and include, but are not limited to, fluorotrichloromethane, trifluoroacetic acid, trichlorotrifluoroethane, and the like. Of these solvents, fluorotrichloromethane is preferred. The solution temperature is preferably maintained in the range of from about $-100°$ C. to about 100° C. during the reaction.

The telomerization reaction can be carried out in a stirred reactor at the indicated temperature conditions. The reaction scheme is illustrated below where n is typically from 1 to 10:

$$CF_3OF + nCF_2=CFCl \longrightarrow F(CF_2CFCl)_nF + \quad (2)$$
$$I$$
$$F_3CO(CF_2CFCl)_nF + F(CF_2CFCl)_nOCF_3 +$$
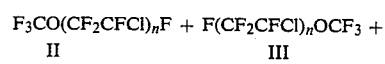
$$II \quad\quad III$$

-continued $$F_3CO(CF_2CFCl)_nOCF_3 \quad IV$$

As can be seen from reaction (2), the telomerization reaction generates a mixture of four discrete telomer species. Species I contains two —F end groups, while species II and III each contain one —OCF$_3$ end group, and species IV contains two —OCF$_3$ end groups. Species II, III and IV are novel telomers.

Although the monomer units of the telomers are depicted as being arranged in a particular order, they are actually randomly joined; that is, they can be joined in either head-to-head or head-to-tail fashion. Reference to a particular structural representation in the specification and claims is for convenience only, and should be construed accordingly.

The composition of the reaction product is believed to be at least partly dependent on solvent effects. For instance, the smaller percentage of species I in comparison to species II, III and IV may be due to the preferential reaction of fluorine atoms with the solvent rather than with the CTFE as intended. The molecular weight distribution of the telomers has also been found to be non-uniform with the lighter wieght products predominating.

The reaction of CTFE with FTM may produce telomers which contain some hydrolyzable chlorine. In this event, it is necessary to fluorinate the telomers to replace the chlorine with fluorine. This results in a product having improved stability and non-reactivity. Chlorine trifluoride (CTF$_3$) is a suitable fluorinating agent for this purpose, although other fluorinating agents such as hydrogen fluoride can be used. The amount of such fluorination required, however, is less than for other CTFE telomers.

Fluoroxytrifluoromethane, which is a starting material in this invention, is a known compound. However, this compound is not readily available in regular channels of commerce. A convenient and inexpensive technique for producing FTM which has been reported in the literature is the reaction of carbon monoxide with excess fluorine. See, for example, G. H. Cady, *Inorganic Synthesis*, Vol. 8, pages 165-170 (1966). This reaction proceeds as follows:

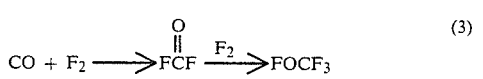

(3)

The telomers prepared according to this invention can be used in a variety of applications, such as fluids for hydraulic systems, pumps and instruments. In such applications, various additives may be used to modify the physical properties of the telomers. In addition to their inherent non-flammability and corrosion resistance, the telomers of this invention have been found to possess excellent solvent properties in comparison to other CTFE-derived fluids.

The following examples are intended to further illustrate the various embodiments and advantages of the present invention without limiting it thereby. Example 1 illustrates the telomerization and fluorination of CTFE and FTM without a solvent. Examples 2-12 illustrate the telomerization reaction of CTFE with FTM in various solvents.

EXAMPLE 1

Fluoroxytrifluoromethane was passed into a 3-neck flask containing chlorotrifluoroethylene. The flask was equipped with a stirrer and a low temperature thermometer. The reaction temperature was maintained at −78° C. An aliquot of the material produced was reacted with chlorine trifluoride, and found to contain no hydrolyzable chlorine or fluorine in treatment with water, as determined by adding AgNO$_3$ and CaCl$_2$, respectively.

EXAMPLE 2

Following the procedure of Example 1, 0.57 gm/hr. of fluoroxytrifluoromethane was added to a solution of 8.4 grams of chlorotrifluoroethylene in 50 ml. of a fluorotrichloroethylene solvent at 0° C. for 6.5 hours. The solution was degassed and the solvent evaporated yielding 7.21 grams of a liquid product. The product was analyzed using GC/MS and GC, and found to contain telomers having both —F and —OCF$_3$ end-groups.

EXAMPLES 3-12

The procedure of Example 2 was repeated using a variety of reaction conditions. The results are summarized in Table I.

TABLE I

| Example No. | CTFE (gms) | Solvent (mls) | FTM Addition Rate | Time of Addition | Temperature | Wt of Product |
|---|---|---|---|---|---|---|
| 3 | 7.1 | CFCl$_3$(50) | 0.57 gms./hr. | 6.5 hr. | −78° C. | 3.5 gms. |
| 4 | 6.6 | CFCl$_3$(50) | 1.17 gms./hr. | 6.0 hr. | −78° C. | 5.4 gms. |
| 5 | 6.7 | CFCl$_3$(50) | 0.57 gms./hr. | 6.5 hr. | −30 to −35° C. | 5.5 gms. |
| 6 | 6.8 | CFCl$_3$(50) | 1.71 gms./hr. | 6.5 hr. | −35° C. | 2.8 gms. |
| 7 | 8.4 | CFCl$_3$(50) | 0.57 gms./hr. | 6.5 hr. | 0° C. | 7.2 gms. |
| 8 | 7.0 | CFCl$_3$(50) | 1.71 gms./hr. | 6.5 hr. | 0° C. | 5.7 gms. |
| 9 | 6.7 | CCl$_2$FCClF$_2$(50) | 0.57 gms./hr. | 6.5 hr. | −32° C. | 4.2 gms. |
| 10 | 7.8 | CF$_3$CO$_2$H(50) | 0.58 gms./hr. | 6.5 hr. | 0° C. | 6.3 gms. |
| 11 | 105.5 | CFCl$_3$(700) | 5.83 gms./hr. | 7.3 hr. | −78° C. | 57.0 gms. |
| 12 | 101.0 | CFCl$_3$(700) | 5.83 gms./hr. | 8.0 hr. | −78° C. | 90.9 gms. |

The products of Examples 3-12 were analyzed to determine the relative amounts of the individual telomer species (as shown in reaction 2) and the relative distribution of molecular weights (n value). The results are reported in Table II.

TABLE II

| | Telomer Species (%, n = 2) | | | n Value (%) | | |
|---|---|---|---|---|---|---|
| Example No. | I | II & III | IV | 2 | 3 | 4 |
| 3 | 7 | 43 | 50 | 52 | 40 | 7 |
| 4 | 3 | 31 | 66 | 69 | 29 | 2 |
| 5 | 8 | 47 | 44 | 22 | 49 | 29 |
| 6 | 13 | 44 | 43 | 31 | 44 | 25 |
| 7 | 5 | 41 | 54 | 37 | 48 | 15 |
| 8 | 16 | 47 | 36 | 32 | 41 | 27 |
| 9 | 15 | 47 | 38 | 32 | 42 | 26 |
| 10 | 5 | 46 | 59 | 32 | 44 | 24 |
| 11 | 4 | 35 | 62 | 59 | 36 | 5 |

TABLE II-continued

| Example No. | Telomer Species (%, n = 2) | | | n Value (%) | | |
|---|---|---|---|---|---|---|
| | I | II & III | IV | 2 | 3 | 4 |
| 12 | 9 | 46 | 45 | 47 | 43 | 10 |

While various embodiments and exemplifications of this invention have been shown and described in the specification, modifications and variations thereof will be readily appreciated by those skilled in the art. It is to be understood, therefore, that the appended claims are intended to cover all such modifications and variations which are considered to be within the scope and spirit of the present invention.

What is claimed is:

1. A process for producing a mixture of telomers consisting of reacting chlorotrifluoroethylene in liquid form with fluoroxytrifluoromethane in the absence of a solvent.

2. The process of claim 1 wherein the telomerization reaction is conducted at a temperature of less than about −30° C.

3. The process of claim 1 wherein the telomerization reaction is conducted at a temperature in the range of from about 100° C. to about −100° C.

4. The process of claim 1 wherein the telomers are fluorinated by reaction with a fluorinating agent.

5. The process of claim 4 wherein the fluorinating agent is chlorine trifluoride.

6. A process for producing a mixture of telomers consisting of reacting chlorotrifluoroethylene with fluoroxytrifluoromethane in a solvent.

7. The process of claim 6 wherein the solvent is selected from the group consisting of fluorotrichloromethane, trifluoroacetic acid, and trichlorotrifluoroethane.

8. The process of claim 7 wherein the solvent is fluorotrichloromethane.

9. The process of claim 6 wherein the telomerization reaction is conducted at a temperature of from about −100° C. to about 100° C.

10. The process of claim 6 wherein the telomers are fluorinated by reaction with a fluorinating agent.

* * * * *